(12) United States Patent
Sugaya et al.

(10) Patent No.: US 11,193,174 B2
(45) Date of Patent: Dec. 7, 2021

(54) EXOSOMAL NANOG DNA AS A DIAGNOSTIC CANCER MARKER

(71) Applicant: UNIVERSITY OF CENTRAL FLORIDA RESEARCH FOUNDATION, INC., Orlando, FL (US)

(72) Inventors: Kiminobu Sugaya, Orlando, FL (US); Vaidya Manjusha, Oviedo, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 89 days.

(21) Appl. No.: 16/457,067

(22) Filed: Jun. 28, 2019

(65) Prior Publication Data

US 2020/0002771 A1  Jan. 2, 2020

Related U.S. Application Data

(60) Provisional application No. 62/691,043, filed on Jun. 28, 2018.

(51) Int. Cl.
*C12Q 1/6886* (2018.01)
(52) U.S. Cl.
CPC ..... *C12Q 1/6886* (2013.01); *C12Q 2600/156* (2013.01)
(58) Field of Classification Search
CPC ... C12Q 1/6886; C12Q 2600/156; C12Q 1/68
See application file for complete search history.

(56) References Cited

U.S. PATENT DOCUMENTS 9,518,098 B2 * 12/2016 Altaba .................. A61K 38/12

OTHER PUBLICATIONS

Fairbanks et al. G3: Genes, Genomes, Genetics 2.11 (2012): 1447-1457 (Year: 2012).*
Zhang et al. FEBS Journal 273 (2006): 1723-1730 (Year: 2006).*
Wang et al. Clin Trans Oncol. 20 (2017): 906-911 (Year: 2017).*
Rodriguez et al. Oncotarget 6(38) (2015): 10575-40587 (Year: 2015).*
Vaidya et al. PLoS ONE 13(5) (2018): 1-13 (Year: 2018).*
Vaidya et al., "Differential sequences of exosomal NANOG DNA as a potential diagnostic cancer marker", PLoS ONE 13(5) (2018): 1-13 (Year: 2018).*

(Continued)

*Primary Examiner* — Jehanne S Sitton
*Assistant Examiner* — Daniel W Nielsen
(74) *Attorney, Agent, or Firm* — Timothy H. Van Dyke; Wolter Van Dyke Davis, PLLC

(57) ABSTRACT

Provided are methods of detecting cancer in a patient that involve analyzing DNA in extracellular vesicles. Detection may involve screening for an insert in a 3' UTR of NANOGP8 present in extracellular vesicles. A method involves (i) obtaining a biological sample containing extracellular vesicles from the patient; (ii) isolating the vesicles from the biological sample; (iii) detecting an amount of NANOG DNA in the vesicles; (iv) comparing the amount of NANOG DNA in the vesicles with vesicles in a non-cancer cell sample, wherein an increased level of NANOG DNA in the vesicles from the patient as compared to the non-cancer cell sample provides a positive indication of cancer in the patient.

12 Claims, 8 Drawing Sheets

Specification includes a Sequence Listing.

(56) References Cited

OTHER PUBLICATIONS

Henson, "Treatment of Glioblastoma Multiforme", (2006) Arch Neurol 63:337-341 (Year: 2006).*

Chatterjee, S. et al., "Role of 5'- and 3'-untranslated regions of mRNAs in human diseases", Biol Cell, 2009, 101(5): p. 251-262.

Garcia-Romero, N., et al., "DNA sequences within glioma-derived extracellular vesicles can cross the intact blood-brain barrier and be detected in peripheral blood of patients", Oncotarget, 2017, 8(1): p. 1416-1428.

Skog, J., et al., "Glioblastoma microvesicles transport RNA and proteins that promote tumour growth and provide diagnostic biomarkers", Nature Cell Biology, 2008, 10(12): p. 1470-1476.

Thakur, B.K., et al., "Double-stranded DNA in exosomes: a novel biomarker in cancer detection", Cell Research, 2014, 24(6): p. 766-769.

Vaidya, M. et al., "Differential sequences of exosomal NANOG DNA as a potential diagnostic cancer marker", 2018, PloS one, 13(5), e0197782; https://doi.org/10.1371/journal.pone.0197782 ; 13 pages.

Whiteside, T.L., "Tumor-derived exosomes and their role in cancer progression", Advances in clinical chemistry, 2016, 74: p. 103-141.

Zbinden, M., et al., "NANOG regulates glioma stem cells and is essential in vivo acting in a cross-functional network with GLI1 and p53", The EMBO Journal, 2010, 29(15): p. 2659-2674.

* cited by examiner

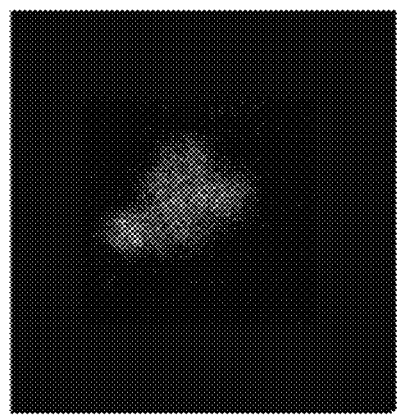
FIG. 1A
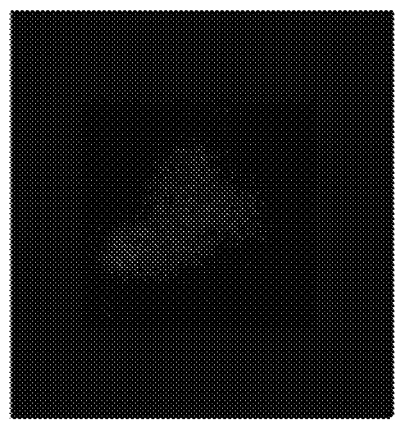
FIG. 1B
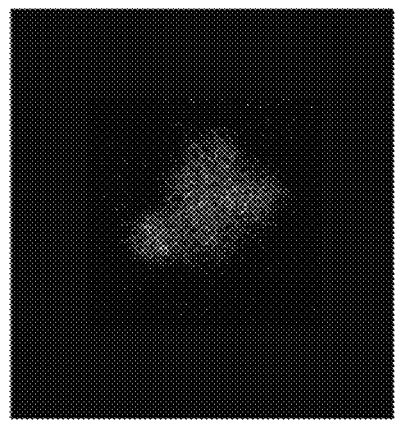
FIG. 1C
1 μm

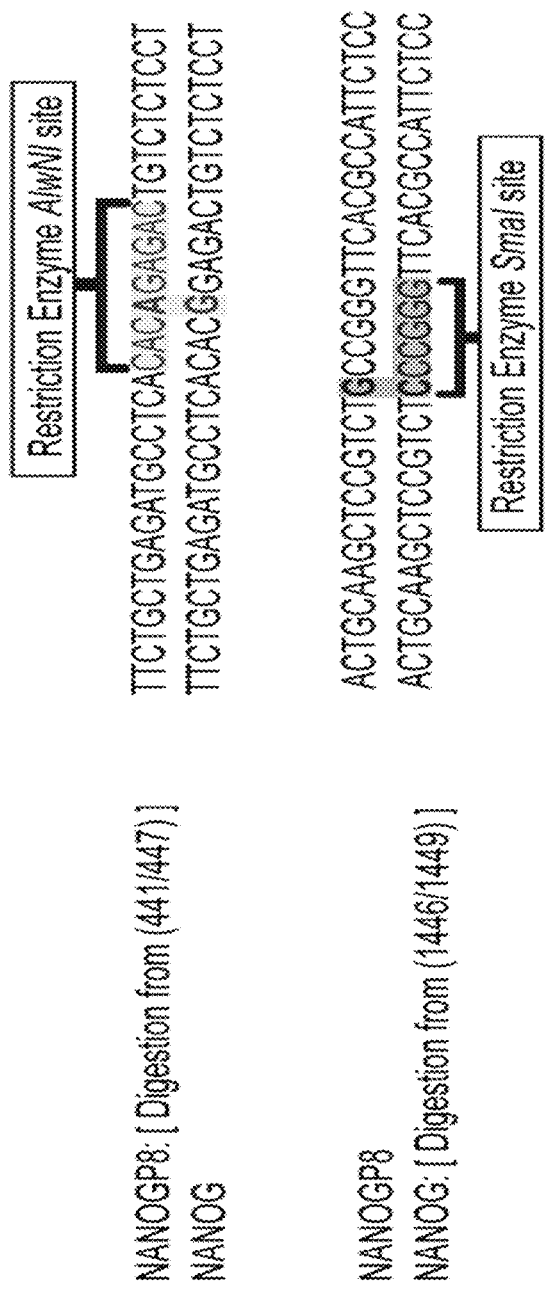

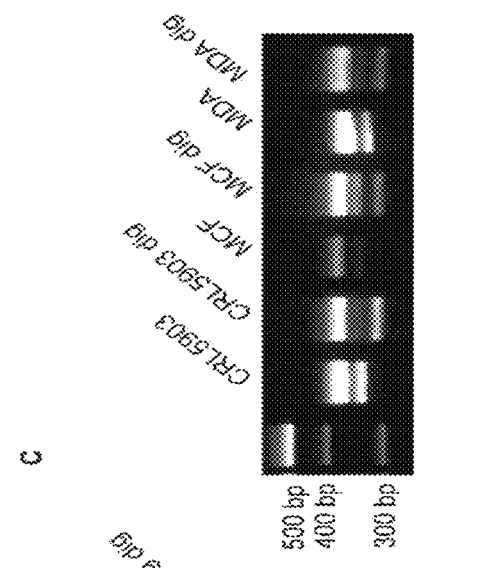
FIG. 4B
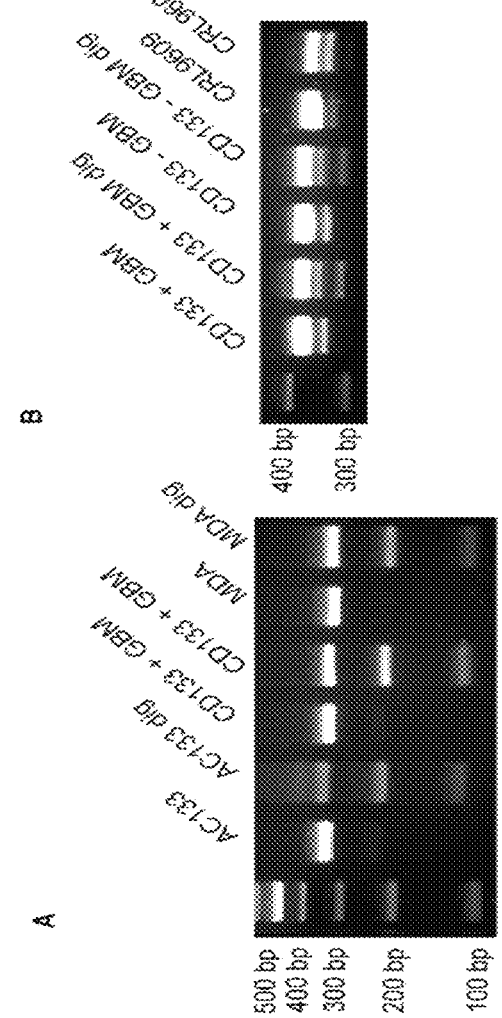
FIG. 4C
FIG. 4A

FIG. 6

| | | | |
|---|---|---|---|
| NANOGP8 mRNA | CCAGAGACGGC | ——————————— | AGCCAAGGTTA |
| PCR Product | CCAGAGACGGC | TTCTATCAATGTTGTCCTTAGC | AGCCAAGGTTA |
| NANOGP1 Intron (4097-4118) | CCAGAGACAGC | TTCTATCAATGTTGTCCTTAAC | AGCCAAGGTTA |
| | | | |
| PCR Product | ACCTTGGCTGC | TAAGGACAACATTGATAGAAGC | CGTCTCTGGCT |
| NANOGP1 Exon (6889-6909) | ACCTTGGCTGC | TAAAGACAAC - TTGATAGAAGC | TGTCTCTGGCT |
| NANOG mRNA CDS | ACCTTGGCTGC | TAAGGACAACATTGATAGAAGC | CGTCTCTGGCT |

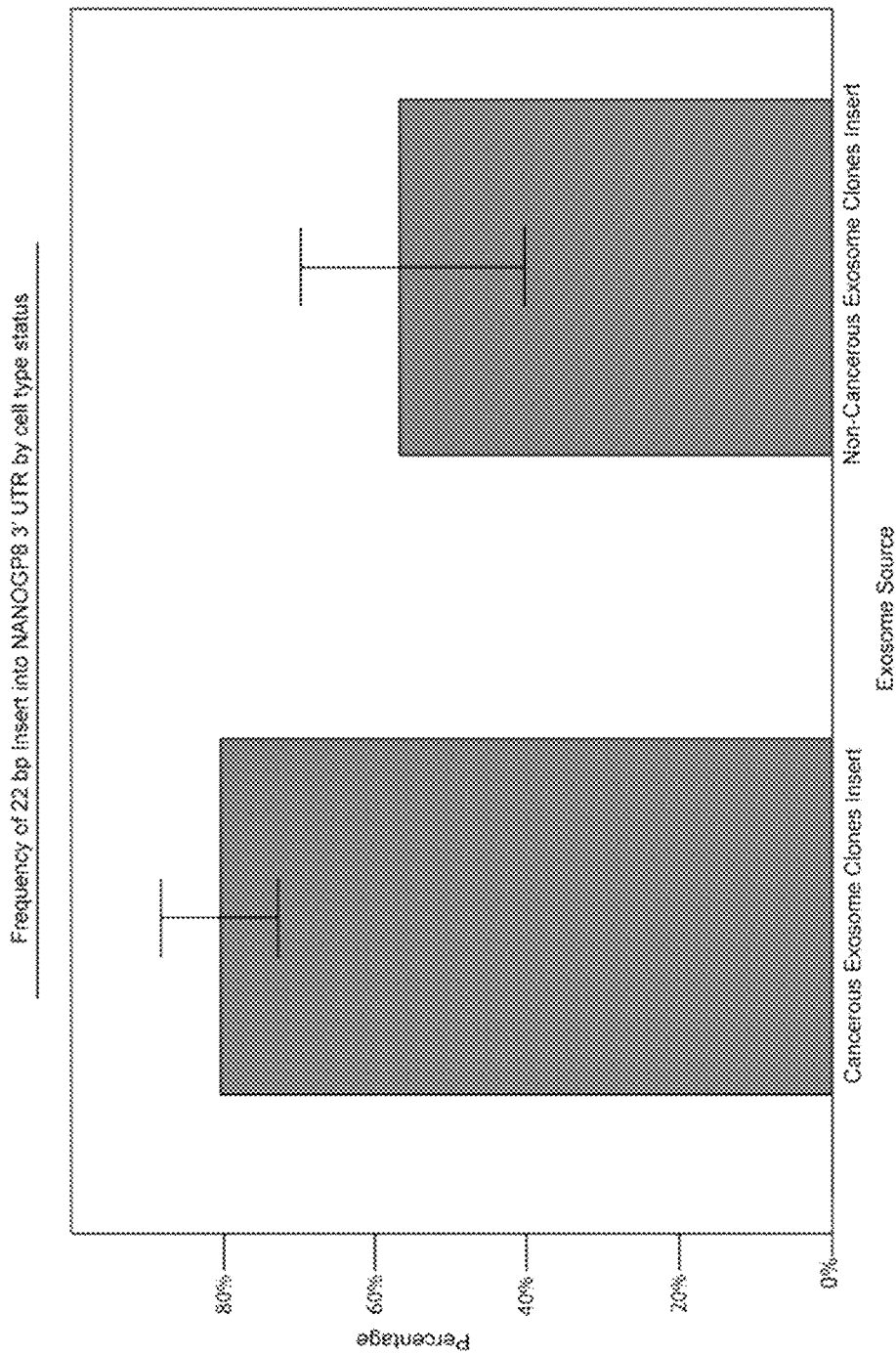

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
aaagcttgcc ttgctttgaa                                          20

<210> SEQ ID NO 2
<211> LENGTH: 19
<212> TYPE: DNA
<213> ORGANISM: Artificial Sequence
<220> FEATURE:
<223> OTHER INFORMATION: primer

```
<400> SEQUENCE: 2
tctgcggagg ctgaggtat                                                  19

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
gtcttctgct gagatgcctc aca                                             23

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
cttctgcgtc acaccattgc tat                                             23

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aaccacgtgt tctggtttcc                                                 20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gatcgagacc atcctggcta                                                 20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggatggtctc gatctcctga                                                 20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cccaatccca aacaatacga                                                 20

<210> SEQ ID NO 9
<211> LENGTH: 37
```

<212> TYPE: DNA
<213> ORGANISM: Homo sapiens

<400> SEQUENCE: 9
ttctgctgag atgcctcaca cagagactgt ctctcct        37

<210> SEQ ID NO 10
<211> LENGTH: 37
<212> TYPE: DNA
<213> ORGANISM: Homo sapiens

<400> SEQUENCE: 10
ttctgctgag atgcctcaca cggagactgt ctctcct        37

<210> SEQ ID NO 11
<211> LENGTH: 37
<212> TYPE: DNA
<213> ORGANISM: Homo sapiens

<400> SEQUENCE: 11
actgcaagct ccgtctgccg ggttcacgcc attctcc        37

<210> SEQ ID NO 12
<211> LENGTH: 38
<212> TYPE: DNA
<213> ORGANISM: Homo sapiens

<400> SEQUENCE: 12
actgcaagct ccgtctcccg ggttcacgcc cattctcc       38

<210> SEQ ID NO 13
<211> LENGTH: 22
<212> TYPE: DNA
<213> ORGANISM: Homo sapiens

<400> SEQUENCE: 13
ccagagacgg cagccaaggt ta        22

<210> SEQ ID NO 14
<211> LENGTH: 44
<212> TYPE: DNA
<213> ORGANISM: Homo sapiens

<400> SEQUENCE: 14
ccagagacgg cttctatcaa tgttgtcctt agcagccaag gtta        44

<210> SEQ ID NO 15
<211> LENGTH: 44
<212> TYPE: DNA
<213> ORGANISM: Homo sapiens

<400> SEQUENCE: 15
ccagagacag cttctatcaa tgttgtcctt aacagccaag gtta        44

<210> SEQ ID NO 16
<211> LENGTH: 44
<212> TYPE: DNA
<213> ORGANISM: Homo sapiens

<400> SEQUENCE: 16
accttggctg ctaaggacaa cattgataga agccgtctct ggct        44

<210> SEQ ID NO 17

```
<211> LENGTH: 43
<212> TYPE: DNA
<213> ORGANISM: Homo sapiens

<400> SEQUENCE: 17
accttggctg ctaaagacaa cttgatagaa gctgtctctg gct                    43

<210> SEQ ID NO 18
<211> LENGTH: 44
<212> TYPE: DNA
<213> ORGANISM: Homo sapiens

<400> SEQUENCE: 18
accttggctg ctaaggacaa cattgataga agccgtctct ggct                   44

<210> SEQ ID NO 19
<211> LENGTH: 22
<212> TYPE: DNA
<213> ORGANISM: Homo sapiens

<400> SEQUENCE: 19
gctaaggaca acattgatag aa                                           22

<210> SEQ ID NO 20
<211> LENGTH: 22
<212> TYPE: DNA
<213> ORGANISM: Homo sapiens

<400> SEQUENCE: 20
taaggacaac attgatagaa gc                                           22
```

EXOSOMAL NANOG DNA AS A DIAGNOSTIC CANCER MARKER

BACKGROUND

Exosomes are extracellular microvesicles (30-100 nm) released by almost all types of cells upon fusion of its multi-vesicular body with the plasma membrane. Known for their role in cell to cell communication, exosomes have demonstrated an ability to unload their contents and contribute to the transformation of normal and stem cells to cancerous states. Previous studies have suggested that RNAs associated with glioblastoma microvesicles may provide diagnostic biomarkers for cancer. Double stranded DNA in cancerous exosomes could also serve as a marker (Thakur et al.).

Glioblastoma multiforme (GBM) is the most common brain cancer, with most patients having an average life expectancy of less than two years following diagnosis. Researchers have previously reported increased methylation of the promoter for O6-methylguanine-DNA methyltransferase and mutations in the gene isocitrate dehydrogenase 1 as possible biomarkers in GBM tissue. However, recent studies have demonstrated that these markers are positively correlated with increased survival of the patient and suggest these targets better serve as prognostic rather than diagnostic markers. Because of this, the identification of accessible and accurate biomarkers to diagnose GBM in its early stages is still needed.

BRIEF DESCRIPTION OF THE DRAWINGS

The present invention is illustrated by way of example, and not by way of limitation, in the figures of the accompanying drawings.

The following figures are illustrative only, and are not intended to be limiting.

FIGS. 1A-C. Confocal Microscopy of HEK 293 exosome clusters. Confocal microscopy images of HEK 293 exosome clusters, demonstrating the preserved integrity of exosome structure of the samples used within this study. FIG. 1A: Green fluorescence from lipophilic stain DiO; FIG. 1B; Red fluorescence from packed RFP (red fluorescent protein); FIG. 1C: Co-localization of both DiO staining and RFP.

FIG. 3. Restriction Enzyme Sequences. Comparison of restriction enzyme cutting sites between NANOGP8 and other NANOG family members. AlwNI site is present and SmaI site is absent in NANOGP8. A single nucleotide at 442 from A to G in NANOG P8 (when compared to other NANOG genes) produces an AlwNI site, while a single nucleotide substitution at 1535 from C to G removes a SmaI site.

FIGS. 4A-C. Typical gel images of exosomal DNA fragments amplified and digested (dig) with AlwNI. FIG. 4A: PCR products from Primer set I. FIG. 4B: PCR products from Primer set II. FIG. 4C: PCR products from Primer set II.

FIG. 5A: fragments from NSCs, GBM and HEK. FIG. 5B: fragments of CRL9609, CRL9609 dig, CRL5903, CRL5903 dig, MCF and MCF dig.

FIG. 6. NANOGP8 insertion sequence analysis. The insert and the surrounding area had high homology to the second intron of NANOGP1 (insertion point 4097, GenBank Accession #NG_006522.3), the fourth exon of NANOGP1 (insertion point 6889, GenBank Accession #NG_006522.3), and NANOG mRNA cds (insertion point 1683, GenBank Accession #AB093576.1).

FIG. 8 22 BP insertion comparison based on cell source status: Analysis demonstrated a comparative result of $\bar{x}=0.8036$ with $\sigma=\pm0.4009$ for cancerous cell derived exosomes, versus $\bar{x}=0.5768$ with $\sigma=\pm0.5038$ for noncancerous cell derived exosomes (with 1=insertion present and 0=insertion absent). The usage of a confidence interval at $C=0.85$ produces intervals of (0.7254, 0.8818) and (0.4302, 0.7237) for cancerous and noncancerous derived exosomes, respectively.

BRIEF DESCRIPTION OF SEQUENCE LISTING

Figure 2:
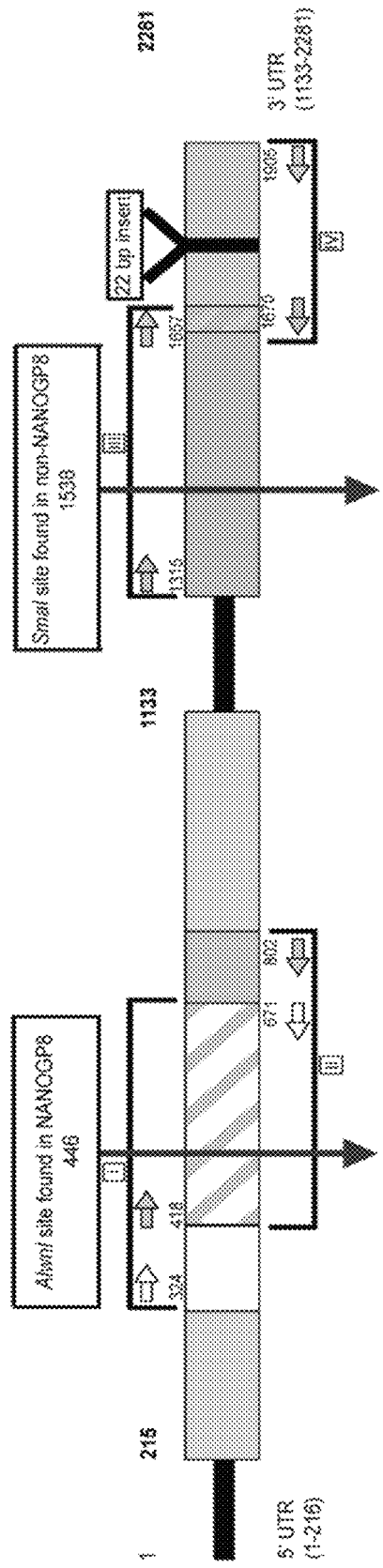
FIG. 2. NANOGP8 Gene and Primer Map. Primer sequences (I-IV) and locations of their PCR products in NANOGP8 gene (GenBank Accession #NG_004093.3). PCR products with primer pair IV frequently had an insertion of a 22 bp fragment at position 1773 in the 3' UTR of NANOGP8 mRNA (GenBank Accession #NM_001355281.1).

SEQ ID NO: 1 Primer sequence for NANOGP8
SEQ ID NO: 2 Primer sequence for NANOGP8
SEQ ID NO: 3 Primer sequence for NANOGP8
SEQ ID NO: 4 Primer sequence for NANOGP8
SEQ ID NO: 5 Primer sequence for NANOGP8
SEQ ID NO: 6 Primer sequence for NANOGP8
SEQ ID NO: 7 Primer sequence for NANOGP8
SEQ ID NO: 8 Primer sequence for NANOGP8
SEQ ID NO: 9 Portion of NANOGP8 showing AlwNI restriction site.
SEQ ID NO: 10 Portion of NANOG gene
SEQ ID NO: 11 Portion of NANOGP8 showing SmaI restriction site.
SEQ ID NO: 12 Portion of NANOG gene
SEQ ID NO: 13 Portion of NANOGP8 transcript at a location showing absence of 22 bp.
SEQ ID NO: 14 PCR product from exosomal DNA
SEQ ID NO: 15 Portion of NANOGP1 intron (4097-4118)
SEQ ID NO: 16 PCR product from exosomal DNA
SEQ ID NO: 17 Portion of NANOGP1 exon (6889-6909)
SEQ ID NO: 18 NANOG mRNA CDS
SEQ ID NO: 19 sequence of 22 base-pair insert
SEQ ID NO: 20 sequence of 22 base-pair insert

DETAILED DESCRIPTION

Overview:

Glioblastoma multiforme (GBM) is the most common type of brain cancer, providing an average life expectancy of less than two years from diagnosis. Increased methylation of the promoter for O6-methylguanine-DNA methyltransferase and mutations in the gene isocitrate dehydrogenase 1 are typically found in GBM tissue, and were previously thought to be useful as biomarkers for GBM. However, it appears that these markers are positively correlated with increased survival of the patient, suggesting that these targets better serve as prognostic rather than diagnostic markers. While these biomarkers are currently used for GBM diagnostics, wherein the markers are positively correlated with increased survival of patients, identification of accessible and accurate biomarkers to diagnose GBM in its early stages is still needed.

NANOG, the DNA binding homeobox transcription factor involved in maintaining the stemness of embryonic stem cells, has been identified herein as an ideal biomarker for the identification of cancer stem cells. Increased expression levels of NANOG have been found in GBM cancer stem cells. As discovered herein, DNA associated with exosomes has been found to be produced not only by cancerous cells but also by normal cells. Consequently, modifications of exosomal DNA have been developed herein as being important diagnostic markers for cancer.

Definitions:

Where the definition of terms departs from the commonly used meaning of the term, applicant intends to utilize the definitions provided below, unless specifically indicated.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising."

The term "about" or "approximately" is meant to denote up to a 5, 6, 7, 8, 9, or 10 percent variance in the stated value or range. For example, about 2 includes values of 1.9 to 2.1.

As used herein, "extracellular vesicles" encompasses "exosomes," or "microvesicles (MVs)," which are released by almost all types of cells upon fusion of its multi-vesicular body with a plasma membrane of the cell, in some embodiments. The term "extracellular vesicles" may include both exosomes and MVs. Extracellular vesicles are present in many, if not all, eukaryotic fluids, including blood, urine and cultured medium of cell cultures. Extracellular vesicles, in particular exosomes or MVs, are known for their role in cell to cell communications and have demonstrated an ability to unload their contents and contribute to the transformation of normal and stem cells to cancerous states. Microvesicles, for example, can be formed by a variety of processes, including the release of apoptotic bodies, the budding of microvesicles directly from the cytoplasmic membrane of a cell, and exocytosis from multivesicular bodies. For example, extracellular vesicles are commonly formed by their secretion from the endosomal membrane compartments of cells as a consequence of the fusion of multivesicular bodies with the plasma membrane. The multivesicular bodies (MVBs) are formed by inward budding from the endosomal membrane and subsequent pinching off of small vesicles into the luminal space. The internal vesicles present in the MVBs are then released into the extracellular fluid as so-called exosomes or extracellular vesicles.

As part of the formation and release of extracellular vesicles, unwanted molecules are eliminated from cells. However, cytosolic and plasma membrane proteins are also incorporated during these processes into the extracellular vesicles, resulting in extracellular vesicles having particle size properties, lipid bilayer functional properties, and other unique functional properties that allow the vesicles to potentially function to carry their payload.

According to one embodiment, extracellular vesicles are isolated from a subject, from a biological sample and are tested for the presence of NANOG. In one particular example, the extracellular vesicles are isolated from a biological sample, and are tested for the presence of NANOGP8, a NANOG associated pseudogene.

As used herein, the term "isolating," or "to isolate," refers to any artificial (i.e., not naturally occurring) process for treating a starting material, where the process results in a more useful form of a molecule or structure of interest (e.g. extracellular vesicles) that is in the starting material. The "more useful form" of the molecule or structure of interest can be characterized in a variety of ways, no one of which is limiting. For example, as used herein, certain embodiments provide methods for isolating extracellular vesicles from a biological sample from a subject, wherein the biological sample may include cancer cells. These cells may include cancer stem cells, breast cancer stem cells, lung cancer stem cells or GBM cancer stem cells. The process for isolating can result in:

(i) the molecule of interest or structure having a greater concentration in the isolated form compared to the starting material (e.g., concentrating), (ii) the removal of any amount or any type of impurities from the starting material (e.g., purifying), (iii) an increase in the ratio of the amount of molecule or structure of interest to the amount of any undesired component in the starting material (e.g., enriching), (iv) any artificial process for removing a molecule or structure of interest from its natural source or location;

(v) any artificial process for separating a molecule or structure of interest from at least one other component with which it is normally associated (e.g., purifying), or (vi) any combination of (i), (ii), (iii), (iv) or (v).

Similarly, as used herein, the term "isolated" generally refers to the state of the molecule or structure of interest after the starting material has been subjected to a method for isolating the molecule of interest. That is to say, isolating a molecule of interest from a starting material will produce an isolated molecule. For example, the methods of the invention are used to produce preparations of isolated extracellular vesicles. In some embodiments, the extracellular vesicles include microvesicles MVs. These preparations of microvesicles have been isolated from their natural source, for example, from urine, or from conditioned cell culture media.

As used herein, the term "purifying" or "to purify" a molecule or structure of interest refers to a process for removing at least one impurity or contaminant from a starting material. For example, purifying a molecule of interest from a starting material refers to a process for removing at least one impurity from the starting material to produce a relatively more pure form of the molecule of interest.

As used herein, the term "substantially purified" refers to molecules or structures of interest that are removed from their natural environment or from a starting material (i.e., they are isolated) and where they are largely free from other components with which they are naturally associated or substantially free of other components that may render future use or study sub-optimal, difficult or impossible.

As used herein, the terms "purified" or "partially purified" refers to molecules or structures of interest that are removed from either (1) their natural environment, or from (2) a starting material (i.e., they are isolated), and where (a) at least one impurity from the starting material has been removed, or (b) at least one component with which the molecule is naturally associated has been removed. A "purified" or "partially purified" molecule may still contain additional components that may render future use or study of the molecule sub-optimal, difficult or impossible.

As used herein, the term "enriching" (and "enriched" and the like) refers to a process whereby a molecule of interest that is in a mixture has an increased ratio of the amount of that molecule to the amount of other undesired components in that mixture after the enriching process as compared to before the enriching process.

A "therapeutically effective amount" refers to an amount which, when administered in a proper dosing regimen, is sufficient to reduce or ameliorate the severity, duration, or progression of the disorder being treated (e.g., cancer), prevent the advancement of the disorder being treated (e.g., cancer), cause the regression of the disorder being treated (e.g., cancer), or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

The term "cancer" as used herein means is intended to include any neoplastic growth in a patient, including an initial tumor and any metastases. The cancer can be of the liquid or solid tumor type. Liquid tumors include tumors of hematological origin (hematological cancer), including, e.g., myelomas (e.g., multiple myeloma), leukemias (e.g., Waldenstrom's syndrome, chronic lymphocytic leukemia, other leukemias), and lymphomas (e g, B-cell lymphomas, non-Hodgkins lymphoma). Solid tumors can originate in organs, and include cancers such as lung, breast, prostate, ovary, colon, kidney, and liver.

The term "biological sample", as used herein, includes a tissue or tissue homogenate, blood or blood component (e.g. plasma, serum, red blood cells, peripheral immune cells) or other fluid sample (tears, urine, semen, vaginal fluid, wound exudate, sweat, sputum, etc.), cells or a cell culture sample. Tissue may be obtained by biopsy or related extraction. Blood is typically obtained by venipuncture. In a specific example, tissue includes neuronal tissue expected of containing cancer cells.

The term "cancer cell" as used herein means a cell that shows aberrant cell growth, such as increased cell growth. A cancerous cell may be a hyperplastic cell, a cell that shows a lack of contact inhibition of growth in vitro, a tumor cell that is incapable of metastasis in vivo, or a metastatic cell that is capable of metastasis in vivo. A cancer cell also includes a cancer stem cell.

As used herein, the term "concentrating" refers to a process whereby a molecule or structure of interest that is in a mixture that has been subjected to that process has a greater concentration after the process as compared to the concentration of the molecule in the mixture before the process.

As used herein, the term "depleted" refers to a mixture containing an undesirable component, where that undesirable component has been (i) completely removed from the mixture, (ii) sufficiently removed from the mixture to be undetectable, or (iii) partially removed from the mixture such that its concentration in the mixture is significantly reduced. For example, a sample that has been depleted of endogenous microvesicles may contain no microvesicles, or may contain no detectible microvesicles, or may contain a reduced level of microvesicles compared to the untreated sample.

As used herein, the term "apoptotic body" refers to a subset of circulating microvesicles that are produced as a result of apoptotic cell destruction. As used herein, it is not intended that an apoptotic body of the invention be limited by any particular size or size range.

The terms "treat", "treating" or "treatment of" as used herein refers to providing any type of medical management to a subject. Treating includes, but is not limited to, administering a composition to a subject using any known method for purposes such as curing, reversing, alleviating, reducing the severity of, inhibiting the progression of, or reducing the likelihood of a disease, disorder, or condition or one or more symptoms or manifestations of a disease, disorder or condition.

The term "primer" means a short nucleic acid sequence that can be paired with one strand of DNA and provides a free 3'OH end at which a DNA polymerase starts synthesis of a deoxyribonucleotide chain.

The term "promoter" means a region of DNA involved in binding of RNA polymerase to initiate transcription.

As used herein, the term "an amount" refers to a statistically significant amount.

As used herein, the term "NANOG DNA" refers to a DNA sequence pertaining to a NANOG gene or a portion thereof. In a specific example, the NANOG gene is NANOGP8.

Detailed Description of Exemplary Embodiments

NANOG is found in increased expression levels in GBM cancer stem cells. It has been identified herein that NANOG is a biomarker for the identification of cancer stem cells. The NANOG family includes original NANOG gene and ten associated pseudogenes (P1-P10). Not only has NANOG expression been found in increased levels in GBM cancer stem cells, but increased expression of NANOG has also been found in other cancer stem cells including breast and lung cancer. Moreover, NANOG DNA has been found in exosomes.

It has been identified herein that NANOG pseudogene 8 (NANOGP8) participates in the reprogramming of normal cells into cancerous states, therefore, NANOGP8 is identified herein as promoting cancer stem cell phenotype. Ergo, according to one embodiment herein, microvesicles are isolated from a biological sample from a subject and are tested for the presence of NANOG. In a more particular embodiment, microvesicles are isolated from a biological sample from a subject and are tested for the presence of NANOGP8. When an amount NANOGP8 from a biological sample from a patient is higher than an amount of NANOGP8 in a non-cancer cell, cancer is detected in the patient.

As found herein, a sequence analysis of exosomal DNA amplified with a NANOGP8 specific primer set frequently showed an insertion of a 22 bp sequence into the 3' UTR. The occurrence rate of this insertion was significantly higher in exosomal DNA clones from cancer cells as compared to normal cells. Analysis of exosomal DNA sequences of NANOG can be used to establish diagnosis for cancer, which would be otherwise inaccessible through noninvasive or minimally invasive techniques (as in GBM), and this process will further elucidate the mechanisms of cancer formation, progression, and metastasis. Mixed populations of NANOG DNA associated with exosomes have been identified and have shown preferential modulations in the sequences from cancer samples, which allows for the detection of traditionally inaccessible cancers (i.e. GBM) through minimally invasive techniques.

The critical roles of NANOG and NANOGP8 in cancer progression and the identification of the association of these genes with exosomes allows for exosomal NANOG to function as a powerful diagnostic biomarker. Variations in NANOG/NANOGP8 gene sequences in exosomal DNA, including an insertion into the 3' UTR and a complete absence of certain gene regions, present novel characteristics. Because extracellular vesicles, including exosomes, are capable of crossing the blood brain barrier, they are detectable in the peripheral blood via minimally invasive techniques. Thus, the novel cancer screening method embodiments described herein, including isolating exosomal NANOG DNA provides an ability to detect cancer, particularly in restricted locations (i.e. GBM).

Treatment

Method of treating cancer, as described herein, include traditional tumor resection, chemotherapies, immunotherapy and radiotherapy methods, and a combination thereof.

Standard of care for glioblastoma treatment currently involves surgery, followed by standard radiotherapy with concomitant and adjuvant chemotherapy with temozolomide. For patients with recurrent GBM, Avastin (Bevacizumab) is approved, either alone or combination with temozolomide and radiation.

Immunotherapeutic approaches include stimulation of an immune response is dependent upon the presence of antigens recognized as foreign by the host immune system. Immunotherapy includes using a host's immune system to intervene in tumor growth. Various mechanisms of harnessing both the humoral and cellular arms of the immune system are currently explored for cancer immunotherapy.

Immunotherapeutic approaches may include cancer-based vaccines, immune checkpoint inhibitors, CAR T-cell therapies, cytokines, or antibodies targeted to the particular cancer at issue (e.g. GBM), in some examples.

Materials and Methods

Cell Culture

Human Neuronal Stem Cells or F-HNSC (procured as Fetal-derived human neural progenitor cells from Lonza) and Glioblastoma Multiforme cells (GBM) were grown in suspension cultures. Primary GBM was prepared by dissociation of human brain tumor patient specimens in accordance with a protocol approved by Florida Hospital Institutional Review Board. The subjects were given informed consent and HIPPA regulations were strictly followed. For proliferation, the cells were cultured in HNSC media containing Heparin 5000 U (0.5 U/mL), EGF—20 ng/mL, bFGF—20 ng/mL and 2% B27 stock mixed in DMEM/F12. To differentiate these cells, the cells were cultured in NT2 (NTERA-2 human embryonal carcinoma cell line) media containing DMEM-F12 supplemented with 10% exosome-depleted FBS. Following the manufacturer's protocol, the cancer stem cells were separated from proliferating GBM cells using CD133 conjugated magnetic beads (Miltenyi Biotec, CD133 microbeads, human, Mat. No. 120-000-312). HEK293 cells (ATCC) were cultured in DMEM containing 10% exosome-depleted FBS, L-glutamine, and 100× non-essential amino acids. Primary umbilical cord blood derived AC133 positive endothelial progenitor cells (AC133) were cultured in hematopoietic progenitor media containing 500 µL of the cytokine FLT3 (fms like tyrosine kinase 3), 500 µL uL of the cytokine SCF (stem cell factor) and 100 µL of the cytokine TPO (thrombopoietin). All types of media were supplemented with penicillin and streptomycin (100 U/mL of each). The following spent media was also used: Conditioned BMEM media for normal bronchial epithelial cells (CRL9609), conditioned BMEM media for normal breast epithelial cells (MCF-10A), conditioned HITES media for small cell lung cancer (CRL5903), and conditioned DMEM media for triple negative breast cancer (MDA-MB-231) cells.

Exosome Isolation

The spent media was centrifuged at 10000×g for 30 minutes to remove cell debris. Exosomes were isolated from conditioned culture media using a modified PEG-NaCl precipitation method [13]. 10 mL of supernatant was used to precipitate exosomes through the addition of 5 mL of 20% PEG and 200 µL of 7.5 M NaCl and subsequent overnight incubation at 4° C. The following day, the supernatant was centrifuged at 10000×g for 60 minutes and the exosome pellet was re-suspended in 1×PBS (pH 7.4, sans Calcium and Magnesium). Using CD63 conjugated magnetic beads [Invitrogen by Thermo Fisher Scientific Exosome—Human CD63 Isolation/Detection (from cell culture media), Ref-10606D], the exosomes were further purified following the manufacturer's protocol.

Polymerase Chain Reaction and Electrophoresis

The exosomes were used directly in place of template without DNA extraction. Using High-Performance GoTaq® G2 DNA Polymerase (Promega), the PCR reactions were set up as follows: 94°—5 minutes, (denaturation: 94°—0:30 minutes, annealing: 55°—0:30 minutes, Extension: 72°—2:00 minutes)×30, 72°—10 minutes. The PCR products were run on 1.5% Agarose gel in 1×TAE buffer.

Restriction Enzyme Digestion of the PCR Products

The DNA with extracted with the QIAquick Gel Extraction Kit (Qiagen), using the manufacturer's protocol. 1 µg of amplicon DNA was digested with restriction enzymes AlwNI (also known as Cail), and SmaI (both ThermoFisher, Fast Digest enzymes) with Fast Digest buffer, at 37° C. for five minutes and run on 3% Agarose gel in 1×TAE buffer.

Cloning of PCR Products in pCR4TOPO-TA Vector

Following the manufacturer's protocol, the PCR products were ligated with the vector, transformed into chemically competent E. coli (Stbl3) cells, and selected on LB with ampicillin (100 µg/mL). Upon overnight incubation at 37°, the colonies were picked, grown in LB with Ampicillin, and the DNA was extracted using QIAprep Spin Miniprep Kit. The clones were digested with Fast Digest (FD) restriction enzyme EcoRI for five minutes at 37° C. and run on 1.5% Agarose gel in TAE buffer.

Exosome Sample Preparation for Imaging

To confirm the integrity of the purified exosomes' structure, we transfected HEK293 cells with XPack MSCV-XP-RFP-EF1 α-Puro vectors (SBI) to express red fluorescent protein (RFP) on the inner surface of the exosomal membrane. Using transfection reagent Lipofectamine® 2000, ~80% confluent HEK293 cells were transfected with 10 µg of plasmid DNA following the manufacturer's protocol. Within 24 hours, the HEK293 cells were observed for RFP and exosomes were collected according to the protocol previously described. The green fluorescent, lipophilic carbocyanine DiO dye (ThermoFisher Scientific) was reconstituted using the manufacturer's protocol. Exosomes were incubated at room temperature for one hour with the stain. Using exosome spin column (Invitrogen by Life Technologies, exosome spin columns, mw 3000, Ref. 4484449), excess unbound dye was removed.

Confocal Imaging

To prepare the samples for confocal microscopy, glass slides were coated with poly L-Ornithine. 50 µL of the DiO stained, RFP packed HEK293 exosome suspension was smeared. After letting the slide dry for five minutes, a cover slip was placed and sealed with transparent acetone. The stained exosomes were imaged using the Zeiss 710 with the Zeiss AxioObserver microscope and the objective plan apochromat 63×/1.40× Oil DIC M27. Green fluorescence was detected at an excitation wavelength setting of 488 nm and emission wavelength setting of 542 nm. Red fluorescence was detected at an excitation wavelength setting of 543 nm and emission wavelength setting of 675 nm.

Statistics

To analyze the occurrence rate of the 22 base pair insertion into the 3' UTR of NANOGP8, one-way ANOVA was performed. To identify the significance of this variation between cancer cell derived exosomes and non-cancer cell derived exosomes, one-way ANOVA was followed by post hoc analysis via Student-Newman-Keuls tests.

Results

The gene fragments associated with PEG-NaCl precipitated exosomes were directly amplified by PCR without DNA isolation using primer sets described (FIG. 2). The identities of the PCR products were confirmed through restriction fragment length polymorphisms (RFLP) analysis by the identification of AlwNI or SmaI digestion (FIG. 3). Primer sets I and II amplified regions containing the AlwNI site unique for NANOGP8 at nucleotide position 446 (GenBank Accession: 388112). The difference in binding positions between primer sets I and II is a 94 bp shift in the forward primer and 131 bp shift in the reverse primer. Primer set III amplified a region containing the SmaI restriction enzyme site unique for NANOG at position 1457 (GenBank Accession: 79923). Primer set IV is specific for a region in the 3' UTR of NANOGP8 [14,15]. A summary of the results, including the presence or absence of NANOGP8 based on cell source and primer set, is reflected in Tables 1A-B.

Both undigested (347 bp) and digested (225 bp and 122 bp) products were observed with electrophoresis after extensive AlwNI treatment of the PCR products generated by primer set I in all the samples analyzed (FIG. 4A). Additionally, AlwNI digestion of PCR products amplified by primer set II showed undigested (384 bp) and digested (356 bp) products, but the presence of a small 28 bp fragment was not detectable in all exosome samples (FIGS. 4B,4C). In addition to the gel electrophoresis, the sequence of the PCR products was analyzed by a M13 sequencing primer after cloning the PCR fragments into pCR4TOPO-TA vectors. For a given cell type, sequence analysis identified an AlwNI cutting site in some clones but not all indicating that a mixed population of NANOGP8 and other NANOG family members was present in the DNA fragments associated with exosomes.

While primer set II successfully yielded 347 bp PCR products with exosomes isolated from all cell types, primer set I failed to generate PCR products from five sources (HEK293, CD133 negative GBM, CRL9609, CRL5903, and MCF-10A). The absence of a PCR product after such a shift is a result of exosomal NANOG DNA lacking a region containing the 94 base pair sequence. In other embodiments, a lack of a primer binding site for the forward and/or reverse primers, as well as nucleotide polymorphisms at the primer binding site for these five types of exosomes may result in NANOG DNA lacking a region containing the 94 base pair sequence. The cell source specific absences of exosomal NANOGP8 regions therefore serves as a biomarker.

Furthermore, attempts to amplify the full length of NANOG (218-2093 bp) by PCR [16] failed to obtain any product with exosomal DNA isolated from NSCs. This contrasts to when we used cellular DNA of NSCs as the template, which successfully amplified the 1875 bp full

TABLE 1

Tables 1A-B. Summary of PCR Product analyses.

A

| | NSC (Proliferating) | NSC (Differentiating) | GBM (Proliferating) | GBM (Differentiating) | GBM CD133− | GBM CD133+ |
|---|---|---|---|---|---|---|
| I | +/−  | +/− | +/− | +/− | NA | +/− |
|   | D    | D   | D   | D   | R  | D   |
| II | +/− | +/− | +/− | +/− | +/− | +/− |
|    | S   | S   | S   | D   | D   | D   |
| III| +/− | +/− | +/− | +/− | +/− | +/− |
|    | S   | D   | S   | D   | D   | D   |
| IV | 25% | 33% | 75% | 75% | 40% | 60% |
|    | S   | S   | S   | S   | S   | S   |

B

| | HEK293 | AC133 | CRL9609 | CRL 5903 | MCF-10A | MDA-MB-231 |
|---|---|---|---|---|---|---|
| I | NA | +/− | NA | NA | NA | +/− |
|   | R  | D   | R  | R  | R  | D   |
| II | +/− | +/− | +/− | +/− | +/− | +/− |
|    | D   | D   | D   | D   | D   | D   |
| III| −/− | +/− | +/− | +/− | −/− | +/− |
|    | D   | D   | D   | D   | D   | D   |
| IV | 100% | 100% | 60% | 93.33% | 60% | 93.33% |
|    | S    | S    | S   | S      | S   | S      |

Legend:
+/− represents a mixed population of NANOGP8 and other NANOG genes.
−/− represents a complete absence of NANOGP8.
NA: No PCR product was created with the given primer set.
S: PCR product underwent sequence analysis. D: PCR product underwent RFLP analysis.
R: PCR product was re-amplified by PCR to confirm the absence of the target sequence in the sample.
Percentages in row 4 indicate percentage of clones containing the 22 bp insertion.

length NANOG. These results suggest that the DNA associated with exosomes do not contain the full length of NANOG but with regions absent.

Figure 5B:
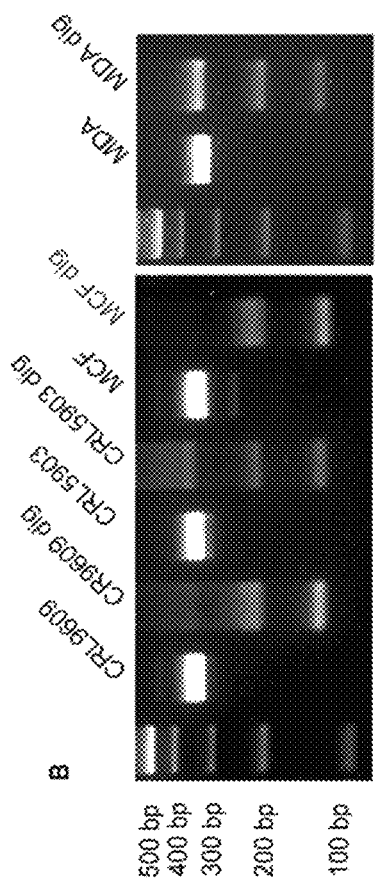
FIGS. 5A-B. Typical gel images of exosomal DNA fragments amplified and digested with SmaI. Red letters indicate a complete digestion by SmaI due to the absence of NANOGP8 in these samples.
Figure 5A:
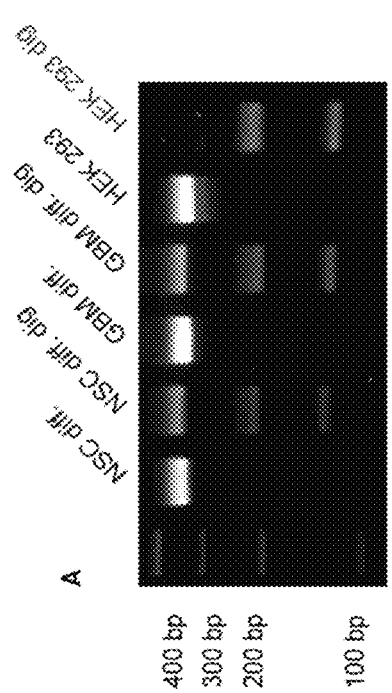

The majority of RFLP analyses of products amplified using primer set III and digested with SmaI showed partial digestion, indicating mixed populations of NANOGP8 and other NANOG family genes. Exosome samples isolated from HEK293 and MCF-10A, however, showed a complete digestion with SmaI through production of 213 bp and 142 bp fragments (FIGS. 5A,5B, red font), suggesting that the DNA fragments associated with these exosomes contain only NANOG (GenBank Accession: 79923) from position 1315-1670.

Sequence analysis of pCR4TOPO-TA vector-cloned PCR products from all samples amplified with primer set IV [17], which is specific to NANOGP8 (GenBank Accession: 388112), showed an insertion of a 22 bp sequence at position 1773. The 22 bp sequence has not been reported in NANOGP8 mRNA (GenBank Accession: NM_001355281.1) nor NANOGP8 genomic DNA (GenBank Accession: NC_000012.12), and thus can be considered an insertion. Although the 22 bp insert is reported in the coding sequence region (cds) of NANOG (GenBank Accession: AB093576.1) and the second intron (4097-4118) as well as the fourth exon (6809-6909) of NANOGP1 (GenBank Accession: 404635), the PCR fragments cannot belong to these genes as primer set IV is NANOGP8 specific. The adjacent sequences, up to 18 bp on either side of the insert, of the PCR products have 94.4% to 100% homology to the corresponding regions of NANOG cds, NANOGP1 intron 2, and NANOGP1 exon 4. The insertion is found to occur within a specific sequence for these genes. Additionally, nucleotide polymorphisms were found in the 22 bp insert between the PCR products and corresponding sequence of the NANOGP1 exon or intron (FIG. 6).

Figure 7:
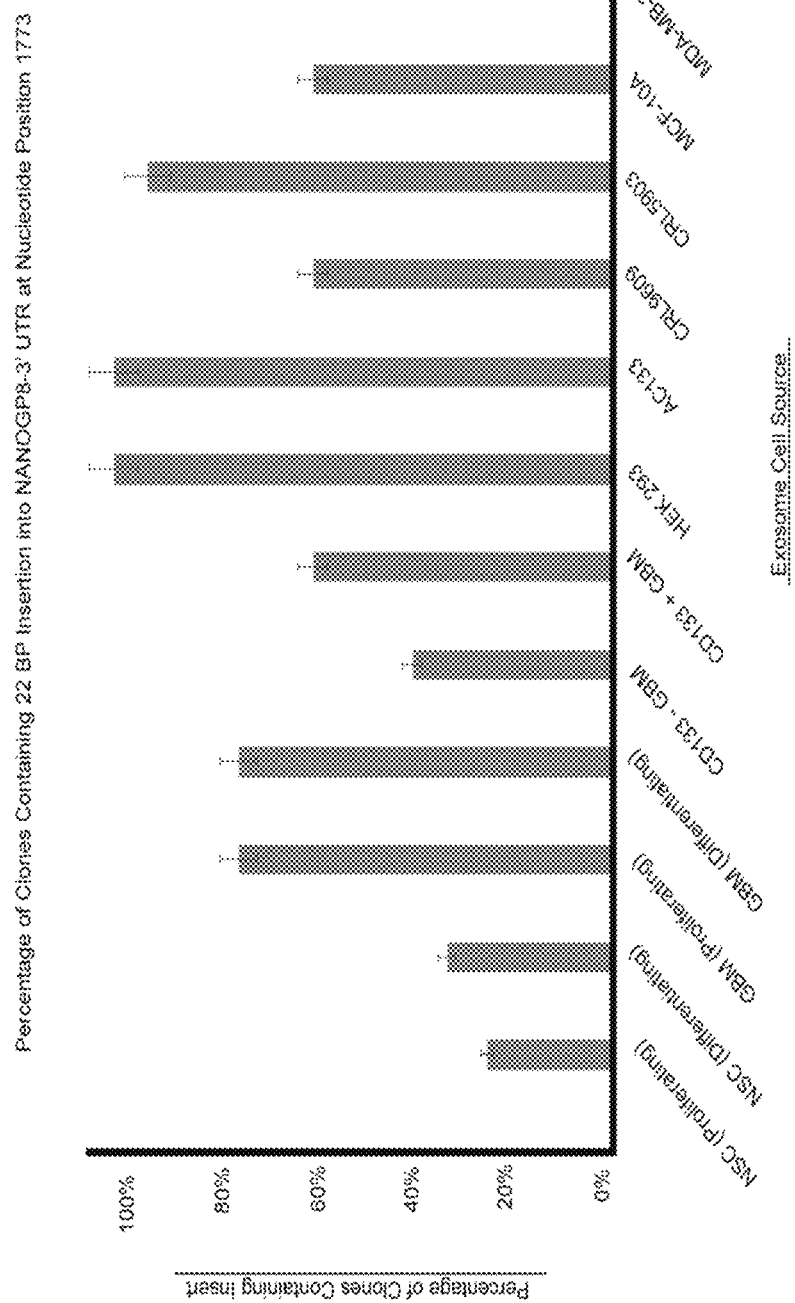
FIG. 7. 22 BP insertion occurrence. Percentage of clones within a cell source containing the 22 bp insert into NANOGP8 3'UTR of exosomal DNA. Specific values are given in Table 1, primer set IV.

The percentage of clones positive for the 22 bp insert varies depending upon the cell source of the exosomes (FIG. 7). To compare the occurrence of the insertion between exosomes derived from cancerous and non-cancerous cells, one-way ANOVA followed by post hoc analysis via Student-Newman-Keuls tests was used. At $\alpha=0.15$, a F value of 4.07 was calculated in addition to $p=0.0313<0.05$. In addition to calculated confidence intervals, analysis of the distribution of the data and mean values for the insertion in cancerous versus noncancerous derived sources demonstrate that the mean values are significantly apart (FIG. 8). The results demonstrate that exosomal DNA derived from cancerous cells have a significantly higher percentage of the insert when as compared to their normal counterparts. Although cell lines MCF 10A and CRL9609 were classified as non-cancerous in this study, these cell lines may exhibit cancer-like properties as these are immortalized cell lines. Such cell lines contain a higher rate of the insertion than normal primary cell lines. Furthermore, the location of this insertion within the 3' UTR of the NANOG gene family indicates its role in modifying translation of the gene. Similarly, the size of the insert (22 bp) indicate mechanisms related to microRNA.

The Vaidya et al. paper [Vaidya, M., Bacchus, M., & Sugaya, K. (2018). Differential sequences of exosomal NANOG DNA as a potential diagnostic cancer marker. *PloS one*, 13(5), e0197782. doi:10.1371/journal.pone.0197782] is related to the above examples and description, and is incorporated herein in its entirety, including the supplemental figures and information.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U. S. C § 112, sixth paragraph. In particular, the use of "step of" in the claims herein is not intended to invoke the provisions of 35 U. S. C § 112, sixth paragraph.

The invention claimed is:

1. A method of screening for cancer in a patient comprising the steps of (i) obtaining a biological sample containing extracellular vesicles from the patient; (ii) isolating the vesicles from the biological sample; (iii) detecting an amount of NANOG DNA in the vesicles; (iv) comparing the amount of NANOG DNA in the vesicles with vesicles in a non-cancer cell sample, (v) identifying an increased level of NANOG DNA in the vesicles from the patient as compared to the non-cancer cell sample, wherein an increased level of NANOG DNA provides a positive indication of cancer in the patient and (vi) administering a cancer therapy, wherein the NANOG DNA comprises NANOGP8 with a 3' untranslated region (UTR) comprising SEQ ID NO: 19 or SEQ ID NO: 20.

2. The method of screening of claim 1, wherein the cancer comprises at least one of: brain cancer, lung cancer, and breast cancer.

3. The method of screening of claim 2, wherein the brain cancer comprises glioblastoma multiforme (GBM).

4. The method of screening of claim 1, wherein isolating the vesicles comprises (i) centrifuging the biological sample to produce a supernatant; and (ii) retrieving the vesicles from the supernatant.

5. The method of screening of claim 1, wherein the detecting comprises sequencing the vesicles DNA, and comparing the sequence with DNA from the non-cancer cell sample, and identifying a 22 base pair insert in a 3' untranslated region of NANOGP8 in the NANOG DNA, wherein the insertion comprises SEQ ID NO: 19 or SEQ ID NO: 20.

6. A method of screening for cancer in a patient comprising the steps of detecting a presence of a 22 bp insert in a 3' untranslated region (UTR) of NANOGP8 gene in extracellular vesicles from a biological sample from the patient, wherein the 22 bp insert comprises SEQ ID NO. 19 or SEQ ID NO. 20, and wherein a presence of the 22 bp insert provides a positive indication of cancer in the patient; and administering a cancer therapy to the patient.

7. The method of screening of claim 6, wherein the cancer comprises at least one of: brain cancer, lung cancer, and breast cancer.

8. The method of screening of claim 7, wherein the brain cancer comprises glioblastoma multiforme (GBM).

9. The method of screening of claim 6, further comprising obtaining the biological sample from the patient and isolating the vesicles from the biological sample.

10. The method of claim 9, wherein isolating the vesicles comprises centrifuging the biological sample to produce a supernatant; and retrieving the vesicles from the supernatant.

11. The method of screening of claim 1, wherein the detecting comprises subjecting DNA from the extracellular vesicles to amplification using SEQ ID NO: 7 and SEQ ID NO: 8 as primers.

12. A method of screening for cancer in a patient comprising the steps of detecting an insert of SEQ ID NO:19 or SEQ ID NO: 20 in a 3' UTR of NANOGP8 gene or portion thereof in extracellular vesicles from a biological sample from the patient, wherein a presence of the insert provides a positive indication of cancer in the patient, and administering a cancer therapy to the patient.

* * * * *